US008658379B2

(12) United States Patent
Hirsch

(10) Patent No.: US 8,658,379 B2
(45) Date of Patent: Feb. 25, 2014

(54) FOLLISTATIN-LIKE PROTEIN-1 AS A BIOMARKER FOR SEPSIS

(75) Inventor: Raphael Hirsch, Iowa City, IA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 13/538,918

(22) Filed: Jun. 29, 2012

(65) Prior Publication Data

US 2013/0011863 A1 Jan. 10, 2013

Related U.S. Application Data

(63) Continuation-in-part of application No. 12/864,709, filed as application No. PCT/US2009/032429 on Jan. 29, 2009, now Pat. No. 8,211,652.

(60) Provisional application No. 61/024,487, filed on Jan. 29, 2008.

(51) Int. Cl.
    *G01N 33/53* (2006.01)
(52) U.S. Cl.
    USPC ............................................. 435/7.1; 435/7.2
(58) Field of Classification Search
    None
    See application file for complete search history.

(56) References Cited

U.S. PATENT DOCUMENTS

| 4,946,778 | A  | 8/1990  | Ladner et al.  |
| 5,143,854 | A  | 9/1992  | Pirrung et al. |
| 5,288,644 | A  | 2/1994  | Beavis et al.  |
| 5,324,633 | A  | 6/1994  | Fodor et al.   |
| 5,432,049 | A  | 7/1995  | Fischer et al. |
| 5,470,710 | A  | 11/1995 | Weiss et al.   |
| 5,492,806 | A  | 2/1996  | Drmanac et al. |
| 5,503,980 | A  | 4/1996  | Cantor         |
| 5,510,270 | A  | 4/1996  | Fodor et al.   |
| 5,525,464 | A  | 6/1996  | Drmanac et al. |
| 5,547,839 | A  | 8/1996  | Dower et al.   |
| 5,580,732 | A  | 12/1996 | Grossman et al.|
| 5,605,690 | A  | 2/1997  | Jacobs et al.  |
| 5,661,028 | A  | 8/1997  | Foote          |
| 5,800,992 | A  | 9/1998  | Fodor et al.   |
| 6,410,232 | B1 | 6/2002  | Holtzman       |
| 7,972,599 | B2 | 7/2011  | Hirsch et al.  |
| 8,211,652 | B2 | 7/2012  | Hirsch         |
| 8,334,274 | B2 | 12/2012 | Hirsch et al.  |
| 2005/0202421 | A1 | 9/2005 | Hirsch et al. |
| 2013/0149712 | A1 | 6/2013 | Hirsch        |

FOREIGN PATENT DOCUMENTS

| EP | 0373203      | 6/1990  |
| EP | 0785280      | 7/1997  |
| WO | WO 94/06476  | 3/1994  |
| WO | WO95/21265   | 8/1995  |
| WO | WO96/31622   | 10/1996 |
| WO | WO97/10365   | 3/1997  |
| WO | WO97/27317   | 7/1997  |
| WO | WO2004/018522| 3/2004  |
| WO | WO 2005/005471| 1/2005 |
| WO | WO2005/032328| 4/2005  |
| WO | WO 2009/097424| 8/2009 |

OTHER PUBLICATIONS

U.S. Appl. No. 12/864,709, filed Nov. 1, 2010.
U.S. Appl. No. 12/864,709, filed Aug. 28, 2012 Certificate of Correction.
U.S. Appl. No. 12/864,709, filed Jul. 26, 2012 Request for Certificate of Correction.
U.S. Appl. No. 12/864,709, filed Jun. 13, 2012 Issue Notification.
U.S. Appl. No. 12/864,709, filed Jun. 4, 2012 Issue Fee Payment.
U.S. Appl. No. 12/864,709, filed Mar. 2, 2012 Notice of Allowance.
U.S. Appl. No. 12/864,709, filed Feb. 17, 2012 Response to Non-Final Office Action.
U.S. Appl. No. 12/864,709, filed Nov. 17, 2011 Non-Final Office Action.
U.S. Appl. No. 12/864,709, filed Sep. 27, 2011 Response to Non-Final Office Action.
U.S. Appl. No. 12/864,709, filed Apr. 27, 2011 Non-Final Office Action.
Bone, et al. (*Leadership Members of ACCP/SCCM*), "American College of Chest Physician/Society of Critical Care Medicine Consensus Conference: Definitions for sepsis and organ failure and guidelines for the use of innovative therapies in sepsis", *Critical Care Medicine*, 20(6):864-874 (1992).
Brown et al., "Control of I kappa B-alpha proteolysis by site-specific, signal-induced phosphorylation", *Science*. 267:1485-1488 (1995).
Chu et al., "IFNgamma deficient C57BL/6 (H-2b) mice develop collagen induced arthritis with predominant usage of T cell receptor IIbeta6 and Vbeta8 in arthritic joints", *Annals of the Rheumatic Diseases*. 62:983-990 (2003).
Clutter et al., "Follistatin like protein-1 is a marker of inflammation", *The Journal of Immunology*, 178:131.31 (2007).
Clutter et al., "Follistatin-Like Protein 1 Promotes Arthritis by Up-Regulating IFN-$\gamma^1$", *TheJournal of Immunology*, 182: 234-239 (2009).
Constantinescu, et al., "Antibodies against IL-12 prevent superantigen-induced and spontaneous relapses of expiremental autoimmune encephalomyelitis", *J Immunol.* 161:5097-104 (1998).
Current Protocols in Molecular Biology (F.M. Ausubel, et al., eds., 1987 including supplements through 2001). Table of contents.
Current Protocols in Nucleic Acid Chemistry, John Wiley & Sons, NY, 2000. Table of Contents retrieved on line from Wiley Online Library on Feb. 24, 2012 http://onlinelibrary.wiley.com/book/10.1002/0471142700/toc.
Diagnostic guidelines for Kawasaki disease. *Circulation*. 103(2):335-336 (2001).
Ehara et al., "Follistatin-related protein gene (FRP) is expressed in the synovial tissues of rheumatoid arthritis, but its polymorphisms are not associated with genetic susceptibility", *Clin Exp Rheumatol.* 22:707-712 (2004).

(Continued)

*Primary Examiner* — Jacob Cheu
(74) *Attorney, Agent, or Firm* — Baker Botts, L.L.P.

(57) ABSTRACT

The present invention relates to methods and kits for diagnosing systemic inflammatory response syndrome or sepsis using levels of FSTL-1.

11 Claims, 2 Drawing Sheets

(56) References Cited

OTHER PUBLICATIONS

Figure 1A:
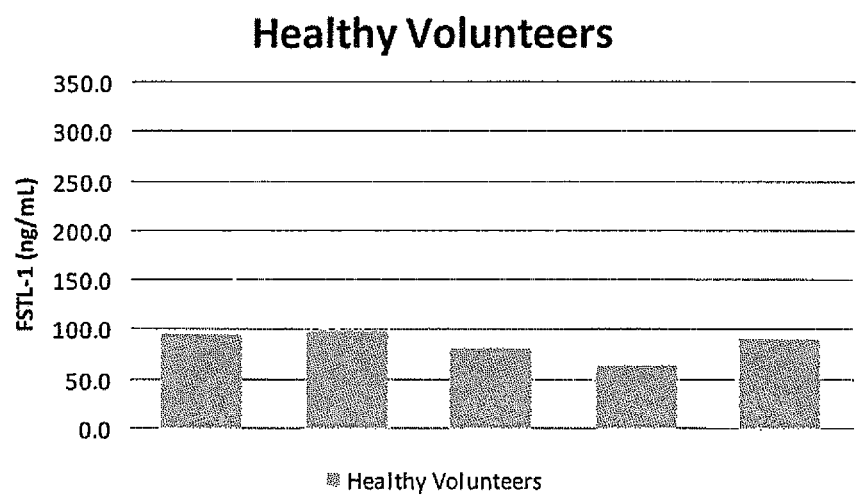

Gett et al., "T cell fitness determined by signal strength", *Nat Immunol*, 4:355-360 (2003).
Hambrock, et al., Journal of Biological Chemistry, 279, 11727, (Mar. 19, 2004).
Hardy et al., "Construction of adenovirus vectors through Crc-lox recombination", *J Virol.* 71(3):1842-1849 (1997).
Harlow and Lane (1988) Antibodies, a Laboratory Manual, Cold Spring Harbor Publications, NY. Table of contents.
Harlow and Lane (1999) Antibodies, a Laboratory Manual, Cold Spring Harbor Press, NY. (Beaucage, et al., eds). Table of contents.
Hughes et al., "Induction of T cell allergy in an experimental model of autoimmunity using non-mitogenic anti-CD3 monoclonal antibody", *J. Immunol.* 153(7):3319-3325 (1994).
Johnston et al., "Regulation of a multigenic invasion programme by the transcription factor, AP-1:re-expression of a down-regulated gene, TSC-36, inhibits invasion", *Oncogene.* 19(47): 5348-58 (2000).
Kawabata et al., "Ameliorative effects of follistatin-related protein/TSC-36/FSTL1 on joint inflammation in a mouse model of arthritis", *Arthritis Rheum.* 50(2):660-668 (2004).
Kim et al., "TNF type 2 receptor (p75) lowers the threshold of T cell activation", *J. Immunol* 167(12):6812-6820 (2001).
Kwak et al., "Reciprocal cross-talk between RANKL and interferon-gamma-inducible protein 10 is responsible for bone-erosive experimental arthritis", *Arthritis Rheum.* 58(5):1332-1342 (2008).
Kubo et al., "Characterization of a monoclonal antibody which detects all murine a[i T cell receptors", *J. Immunol.* 142(8):2736-2742 (1989).
Mashimo et al., "Decrease in the expression of a novel TGF beta1-inducible and ras-recision gene, TSC-36, in human cancer cells", *Cancer Letters.* 113(1-2): 213-219 (1997).
Massague et al., "Controlling TGF-beta signaling", *Genes Development*, 14(6):627-644 (2000).
Miyamae et al., "Follistatin-like protein-1 is a novel proinflammatory molecule", *J Immunol.* 177(7):4758-4762 (2006).
Miyamae et al., "682. Over-Expression of Follistatin-Like Protein Exacerbates Collagen Induced Arthritis", *Molecular Therapy*, 11:S264 (2005).
Molecular Cloning: A Laboratory Manual, Second Edition (Sambrook et al., 1989). Table of contents.
Molecular Cloning: A Laboratory Manual, Third Edition (Sambrook and Russel, 2001). Table of contents.
Moustakas, "Small signalling network", *J. Cell Sci.* 115(Pt. 17):3355-3356 (2002).
Okabayashi et al., "cDNA cloning and distribution of the *Xenopus* follistatin-related protein", *Biochem Biophys Res Commun.* 254(1): 42-48 (1999).
Ohashi et al., "TSC-36 (follistatin-related polypeptide) gene expression in estrogen receptor positive osteoblastic cell line, CDO7F", *Calcif Tissue Int.* 61(5): 400-403 (1997).
PCR: The Polymerase Chain Reaction, (Mullis, et al., eds., 1994). Table of contents.
Shibanuma et al., "Cloning from a mouse osteoblastic cell line of a set of transforming-growth-factor-beta 1-regulated genes, one of which seems to encode a follistatin-related polypeptide", *Eur J Biochemn.* 217(1):13-19 (1993).
Shin et al., "7,12-Dimethylbenz(a)Anthracene Treatment of a *c-rel* Mouse Mammary Tumor Cell Line Induces Epithelial to Mesenchymal Transition via Activation of Nuclear Factor-κB", *Cancer Res*, 66(5):2570-2575 (2006).
Sowders et al., "Follistatin-like gene expression is upregulated in murine collagen induced arthritis", *FASEB Journal Fed. American Soc. For Experimental Biology*, 16(4):A326, (2002).
Sudo et al., "In vitro differentiation and calcification in a new clonal osteogenic cell line derived from newborn mouse calvaria", *J. Cell Biol.* 96(1):191-198 (1983).

Sumitomo et al., "Expression of TGF-ϵ1 inducible gene, TSc-36, causes growth inhibition in human lung cancer cell lines", *Cancer Letters*, 155(1): 37-46 (2000).
Tanaka et al., "Cloning of follistatin-related protein as a novel autoantigen in systemic rheumatic diseases", *Int Immunol.* 10(9):1305-1314 (1998).
Tanaka et al., "Potential preventive effects of follistatin-related protein1TSC-36 on joint destruction and antagonistic modulation of its autoantibodies in rheumatoid arthritis", *Int Immunol.* 15(1):71-77 (2003).
Thornton et al., "DNA microarray analysis reveals novel gene expression profiles in collagen-induced arthritis", *Clinical Immunology.* 105(2):155-168 (2002).
Thornton et al., "NK cells secrete high levels of IFN-gamma in response to in vivo administration of IL-2", *European Journal of Immunology.* 31(11):3355-3360 (2001).
Thornton et al., "Heterogeneous effects of IL-2 on collagen-induced arthritis", *J. Immunol.* 165(3):1557-1563 (2000).
Trojan et al., "Identification of metastasis-associated genes in prostate cancer by genetic profiling of human prostate cancer cell lines", *Anticancer Res.* 25(1A):183-191 (Jan.-Feb. 2005).
Yamada et al., "TNF:TNF-R T-Cell costimulatory pathways in transplantation", *Transplant Pnac.* 33(7-8):3070-3071 (2001).
van Stipdonk et al., "Dynamic programming of $CD8^+$ T lymphocyte responses", *Nat Immunol.* 4(4):361-365 (2003).
Wilson, et al. "Follistatin-like Protein 1 is a Mesenchyme-Derived Inflammatory Protein and May Represent a Biomarker for Systemic-onset Juvenile Rheumatoid Arthritis", *Arthritis & Rheumatism*, 62(8): 2510-2516 (2010).
U.S. Appl. No. 13/758,405, filed Feb. 4, 2013.
U.S. Appl. No. 11/688,779, filed Mar. 20, 2007.
U.S. Appl. No. 13/156,097, filed Jun. 8, 2011.
U.S. Appl. No. 13/758,405, Oct. 30, 2013 Response to Non-Final Office Action.
U.S. Appl. No. 13/758,405, May 31, 2013 Non-Final Office Action.
U.S. Appl. No. 11/688,779, Feb. 19, 2013 Certificate of Correction.
U.S. Appl. No. 11/688,779, May 27, 2011 Issue Fee payment.
U.S. Appl. No. 11/688,779, Mar. 4, 2011 Notice of Allowance and Examiner Interview Summary.
U.S. Appl. No. 11/688,779, Dec. 2, 2010 Response to Non-Final Office Action.
U.S. Appl. No. 11/688,779, Sep. 2, 2010 Non-Final Office Action.
U.S. Appl. No. 11/688,779, Dec. 9, 2009 Amendment and Request for Continued Examination (RCE).
U.S. Appl. No. 11/688,779, Jul. 7, 2009 Final Office Action.
U.S. Appl. No. 11/688,779, Mar. 24, 2009 Response to Non-Final Office Action.
U.S. Appl. No. 11/688,779, Nov. 25, 2008 Non-Final Office Action.
U.S. Appl. No. 11/688,779, Jul. 31, 2008 Response to Restriction Requirement.
U.S. Appl. No. 11/688,779, May 1, 2008 Restriction Requirement.
U.S. Appl. No. 13/156,097, Nov. 12, 2012 Issue Fee payment.
U.S. Appl. No. 13/156,097, Oct. 22, 2012 Notice of Allowance.
U.S. Appl. No. 13/156,097, Sep. 17, 2012 Response to Non-Final Office Action.
U.S. Appl. No. 13/156,097, Jun. 15, 2012 Non-Final Office Action.
U.S. Appl. No. 13/156,097, May 16, 2012 Response to Restriction Requirement.
U.S. Appl. No. 13/156,097, Feb. 16, 2012 Restriction Requirement.
International Search Report and Written Opinion for PCT/US2011/046742, dated Apr. 6, 2012.
International Search Report for PCT/US2007/064441, dated Nov. 15, 2007.
Atli, et al., "eNOS G894T polymorphism and abdominal aortic aneurysms", *Angiology*, 61(2):125-130 (2010).
Aggarwal, et al., "Interleukin-23 Promotes a Distinct CD4 T Cell Activation State Characterized by the Production of Interleukin-17", *The Journal of Biological Chemistry*, 278(3):1910-1914 (2003).
Beiser, et al., "A predictive instrument for coronary artery aneurysms in Kawasaki disease. US multicenter Kawasaki disease study group", *Am. J Cardiol.*, 81(9):1116-1120 (1998).

(56) References Cited

OTHER PUBLICATIONS

Bettelli, et al., "Reciprocal Developmental Pathways for the Generation of Pathogenic Effector $T_H17$ and Regulatory T Cells", *Nature*, 441:235-238 (2006).
Bleesing et al., "the Diagnostic Significance of Soluble CD163 and Soluble Interleukin-2 Receptor α-Chain in Macrophage Activation Syndrome and Untreated New-Onset Systemic Juvenile Idiopathic Arthritis", *Arthritis and Rheumatism*, 56(3):965-971 (2007).
Burns, et al., "Kawasaki Syndrome", *Lancet*, 364(9433):533-544 (2004).
Cole, et al., "The EBV-Hybridoma Technique and its Application to Human Lung Cancer", *Monoclonal Antibodies and Cancer Therapy*, pp. 77-96 (1985).
Cote, et al., "Generation of human monoclonal antibodies reactive with cellular antigens", *PNAS*, 80:2026-2030 (1983).
Fukazawa, et al., "Coronary artery aneurysm induced by Kawasaki disease in children show features typical senescence", *Circ. J.*, 71(5):709-715 (2007).
Galeotti, et al., "Kawasaki Disease: Aetiopathogenesis and therapeutic utility of intravenous immunoglobulin", *Autoimmun Rev.*, 9(6):441-448 (2010).
Genbank Accession No. BC000055 update Jul. 15, 2006, located at http://www.ncbi.nlm.nih.gov/entrez/viewer.fcqi?db=nuccore&id=33990756 last visited on Aug. 8, 2007, 4 pages.
Genbank Accession No. BC028921 updated Jul. 15, 2006, located at http://www.ncbi.nlm.gove/entrez/viewer.fcqi?db=nuccore&id=208100326 last visited Aug. 8, 2007, 3 pages.
Gordon, et al., "When children with Kawasaki disease grow up myocardial and vascular complications in adulthood", *J. Am. Coll Cardiol.*, 54(21):1911-1920 (2009).
Honorati, et al., "High in vivo expression of interleukin-17 receptor in synovial endothelial cells and chondrocytes from arthritis patients", *Rheumatology*, 40:522-527 (2001).
Hwang, et al,, "IL-17 induces production of IL-6 and IL-8 in rheumatoid arthritis synovial fibroblasts via NF-κB- and P13-kinase/Akt-dependent pathways", *Arthritis Research & therapy*, 6(2):R120-R128 (2004).
Ivanov, et al., "The orphan nuclear receptor RORγt directs the differentiation program of proinflammatory IL-17$^+$ T helper cells", *Cell*, 126:1121-1133 (2006).
Iwasa, et al., "Selection of high-risk children for immunoglobulin therapy in Kawasaki disease", *Prog. Clin. Biol. Res.*, 250:543-544 (1987).
Kato, et al., "Long-term consequences of Kawasaki disease. A 10- to 21-year follow-up study of 594 patients", *Circulation*, 94(6):1379-1385 (1996).
Kawasaki, et al., "Pediatric acute febrile mucocutaneous lymph node syndrome with characteristic desquamation of fingers and toes: my clinical observation of fifty cases", *Pediatr. Infect. Dis. J.*, 21(11):1-38 (2002).
Kelly, et al., "Recognition and Management of Macrophage Activation syndrome in Juvenile arthritis", *Curr. Opin. Rheumatol.*, 19(5):477-481 (2007).
Kim, et al., "Up-regulation of IL-23p19 expression in rheumatoid arthritis synovial fibroblasts by IL-17 through P13-kinase-,NF-κB- and p38 MAPK-dependent signalling pathways", *Rheumatology*, 46:57-64 (2007).
Kohler, et al., "Continuous cultures of fused cells secreting antibody of predefined specificity", *Nature*, 256:495-497 (1975).
Kolls, et al., "Interleukin-17 family members and inflammation", *Immunity*, 21:467-476 (2004).
Koren, et al., "Kawasaki disease: Review of risk factors for coronary aneurysms", *J. Pediatr.*, 108(3):388-392 (1986).
Kotake, et al., "IL-17 in synovial fluids from patients with rheumatoid arthritis is a potent stimulator of osteoclastogenesis", *J. Clin. Invest.*, 103(9):1345-1352 (1999).
Kozbor, et al., "The production of monoclonal antibodies from human lymphocytes", *Immunology Today*, 4(3):72-79 (1983).

Lara-Pezzi, et al., Follistatin Gene Expression is elevated in Heart Failure and Decreases Falling Recovery, *Abstracts/Journal of Molecular and Cellular Cardiology*, 42:S145-S161 (2007).
Lara-Pezzi, et al., "Expression of follistatin-related genes is altered in heart failure", *Endocrinology*, 149(11):5822-5827 (2008).
Leonard, et al., "Prevention of experimental autoimmune encephalomyelitis by antibodies against interleukin 12", *J. Exp. Med.*, 181(1):381-386 (1995).
Lin, et al., "Cytokines predict coronary aneurysm formation in Kawasaki disease patients", *Eur. J. Pediatr.*, 152(4):309-312 (1993).
Lubberts, et al., "IL-1-independent role of IL-17 in synovial inflammation and joint destruction during collagen-induced arthritis", *J. Immunol.*, 167:1004-1013 (2001).
The Merck Manuals Online Medical Library, [online]. Whitehouse Station, NJ: Merck Research Laboratories, 2006-2007 [retrieved on Nov. 19, 2007] Retrieved from the internet: <URL: http://www.merck.com/mmpe/print/sec06/ch068/ch068a.htlm>. Sepsis and Septic Shock, pp. 1-5.
Mashimo, et al., "Decrease in the expression of a novel TGF β1-inducible and ras-recision gene, TSC-36, in human cancer cells", *Cancer Letters*. 113(1-2): 213-219 (1997).
Mohan, et al., "Effect of cytokines and growth factors on the secretion of inhibin A. activin A and follistatin by term placental villous trophoblasts in culture", *European Journal of Endocrinology*, 145:505-511 (2001).
Morrison, et al., "chimeric human antibody molecules: Mouse antigen-binding domains with human constant region domains", *PNAS*, 81:6851-6855 (1984).
Nakae, et al., "Suppression of immune induction of collagen-induced arthritis in IL-17-deficient mice", *The Journal of Immunology*, 171:6173-6177 (2003).
Nakamura, et al., "Epidemiologic features of Kawasaki disease in Japan: Results of the 2007-2008 nationwide survey", *J. Epidemiol.*, 20(4):302-307 (2010).
Nakano, et al., "Scoring method for identifying patients with Kawasaki disease at high risk of coronary artery aneurysms", *Am. J. Cardiol.*, 58(9):739-742 (1986).
Negoro, et al., "Successful catheter interventional therapy for acute coronary syndrome secondary to Kawasaki disease in young adults", *Circ. J.*, 76(4):362-365 (2003).
Neuberger, et al., "Recombinant antibodies possessing novel effector functions", *Nature*, 312:604-608 (1984).
Newburger, et al., "The treatment of Kawasaki syndrome with intravenous gamma globulin", *The New England Journal of Medicine*, 315(6):341-347 (1986).
Oppmann, et al., "Novel p19 protein engages IL_12p40 to form a cytokine, IL-23, with biological activities similar as well as distinct from IL-12", *Immunity*, 13:715-725 (2000).
Oshima, et al., "Follistatin-like 1 is an Akt-regulated cardioprotective factor that is secreted by the heart", *Circulation*, 117(24):3099-3108 (2008).
Oshima, et al., "Abstract 1101: Cardio-Protective Action of Follistatin Like-1, a Secreted Anti-Apoptotic Factor Regulated by Akt1", *Circulation*, 116:221 (2007).
Ouchi, et al., "Follistatin-like 1, a secreted muscle protein, promotes endothelial cell function and revascularization in ischemic tissue through a nitric-oxide synthase-dependent mechanism", *J. Biol. Chem.*, 283(47):32802-32811 (2008).
Overbergh, et al., "The use of real-time reverse transcriptase PCR for the quantification of cytokine gene expression", *Journal of Biomolecular Techniques*, 14:33-43 (2003).
Pimiento, et al., "Endothelial nitric oxide synthase stimulates aneurysm growth in aged mice", *J. Vasc. Res.*, 45(3):251-258 (2008).
Printz, et al., "Noncoronary cardiac abnormalities are associated with coronary artery dilation and with laboratory inflammatory markers in acute Kawasaki disease", *J. Am. Coll. Cardiol.*, 57(1):86-92 (2011).
Ravelli, et al., "Preliminary Diagnostic guidelines for Macrophage Activation Syndrome Complicating systemic Juvenile Idiopathic Arthritis", *The Journal of Pediatrics*, 146:598-604 (2005).
Rowley, et al., "New developments in the search for the etiologic agent of Kawasaki disease", *Curr. Opin. Pediatr.*, 19(1):71-74 (2007).

(56) References Cited

OTHER PUBLICATIONS

Segal, et al., "An interleukin (IL)-10/IL-12 Immunoregulatory circuit controls susceptibility to autoimmune disease", *J. Exp. Med.*, 187(4):537-546 (1998).

Simonini, et al., "Macrophage Activation Syndrome/Hemophagocytic Lymphohistiocytosis and Kawasaki Disease", *Pediatr Blood Cancer*, 55:591 (2010).

Song, et al., "Risk factors for Kawasaki disease-associated coronary abnormalities differ depending on age", *Eur. J. Pediatr*, 168(11):1315-1321 (2009).

Standen, et al., "Septic Shock", *The New England Journal of Medicine*, 343(6):447-448 (2000).

Suresh, et al., "Macrophage Activation Syndrome: a Rare complication of Incomplete Kawasaki Disease", *Annals of Tropical Pediatrics*, 3(0):61-64 (2010).

Takeda, et al., "Construction of chimaeric processed immunoglobulin genes containing mouse variable and human constant region sequences", *Nature*, 314:452-454 (1985).

Tamura, et al., "Endothelial damage due to impaired nitric oxide bioavailability triggers cerebral aneurysm formation in female rats", *J. Hypertens.*, 27(6):1284-1292 (2009).

Taubert, et al., "Nationwide survey of Kawasaki disease and acute rheumatic fever", *J. Pediatr.*, 119(2):279-282 (1991).

Terai, et al., "Prevalence of coronary artery abnormalities on Kawasaki disease is highly dependent on gamma globulin dose but independent of salicylate dose", *J. Pediatr.*, 131(6):888-893 (1997).

Veldhoen, et al., "TGFβ in the context of an inflammatory cytokine milieu supports de novo differentiation of IL-17-producing T cells", *Immunity*, 24:179-189 (2006).

Widera, et al., "Circulating Concentrations of Follistatin-Like 1 in Healthy Individuals and Patients with Acute Coronary Syndrome as Assessed by an Immunoluminometric Sandwich Assay", *Clinical chemistry*, 55(10):1794-1800 (2009).

Yea, et al., "Incomplete Kawasaki disease in patients younger than 1 year of age: A possible inherent risk factor", *Eur. J Pediatr.*, 168(2):157-162 (2009).

Zhou, et al., "Identification of a follistatin-related protein from the tick *Haemaphysalis longicornis* and its effect on tick oviposition", *Gene*, 372:191-198 (2006).

FOLLISTATIN-LIKE PROTEIN-1 AS A BIOMARKER FOR SEPSIS

PRIORITY CLAIM

This application is a continuation-in-part of U.S. patent application Ser. No. 12/864,709 having filing/371 date Nov. 1, 2010, now U.S. Pat. No. 8,211,652, which is a national stage application of International Patent Application No. PCT/US2009/032429, filed Jan. 29, 2009 and published in English on Aug. 6, 2009 as WO/2009/097424, which claims priority to U.S. Provisional Application No. 61/024,487, filed Jan. 29, 2008, to all three of which priority is claimed, and the contents of each of which is hereby incorporated by reference in its entirety herein.

GRANT INFORMATION

This invention was made with government support under Grant Nos. RO1HL080926 and RO1AI073556-03S1 awarded by the National Institutes of Health. The government has certain rights in the invention.

1. FIELD OF THE INVENTION

The invention provides for methods and kits for using levels of follistatin-like protein-1 (FSTL-1) as a biomarker for inflammatory diseases including the systemic inflammatory response syndrome (SIRS) and sepsis.

2. BACKGROUND OF THE INVENTION

Follistatin-Like Protein-1 (FSTL-1; also known as FRP or TSC-36) is an extracellular glycoprotein belonging to the BM-40/SPARC/osteonectin family of proteins containing both extracellular calcium-binding and follistatin-like domains. See e.g., U.S. Pat. No. 6,410,232. FSTL-1 was originally cloned from an osteoblastic cell line as a TGF-.beta. inducible gene. M. Shibanuma et al., Eur J Biochem 217, 13 (1993). The protein occurs in two isoforms resulting from differential sialylation. FSTL-1 has been detected in the medium of all osteosarcoma and chondrosarcoma cell lines, and in some cells of the fibroblast lineage. In mice, the highest expression of FSTL-1 has been observed in the lung. J. Mashimo et al., Cancer Lett 113, 213 (1997).

The action of FSTL-1 is unclear, and both proliferative and anti-proliferative effects have been reported. It is thought that FRP may play a role in neuralization during embryogenesis and its expression is upregulated by estrogen. See K. Okabayashi et al., Biochem Biophys Res Commun 254, 42 (Jan. 8, 1999) and T. Ohashi et al., Calcif Tissue Int 61, 400 (November, 1997). In contrast to other BM-40 family members, the extracellular calcium-binding domain of FSTL-1 is non-functional, suggesting that, despite its sequence homology to BM-40, it has evolved clearly distinct properties. H. O. Hambrock et al., Journal of Biological Chemistry 279, 11727 (Mar. 19, 2004). Analysis of prostate cancers has revealed that over-expression of FSTL-1 may be associated with higher metastatic potential. L. Trojan et al., Anticancer Res 25, 183 (January-February, 2005). In contrast, FSTL-1 expression has been extinguished in v-ras-transformed rat fibroblasts, and transfection of FSTL-1 into these cells inhibited in vitro invasion and led to growth inhibition in human lung cancer cells. See I. M. Johnston et al., Oncogene 19, 5348 (Nov. 9, 2000) and K. Sumitomo et al., Cancer Lett 155, 37 (Jul. 3, 2000).

In addition, it has previously been shown that FSTL-1 is highly-upregulated in the joints during the acute phase of collagen-induced arthritis (CIA), most prominently at the junction of synovium and eroding bone, suggesting a role in joint destruction. S. Thornton et al., Clin Immunol 105, 155 (2002).

In 1998, Tanaka et al. cloned FRP from rheumatoid arthritis (RA) synovial tissue and demonstrated the presence of anti-FSTL-1 antibodies in the serum and synovial fluid of RA patients. M. Tanaka et al., International Immunology 10, 1305 (1998). In addition, Tanaka et al. analyzed the mRNA expression and protein expression of FRP in from patients with RA and patients with osteoarthritis (OA) and found that the FRP mRNA expression was higher in RA than in OA synovial samples. Importantly, Tanaka et al. concluded that there was no difference in the protein levels of FRP between these two groups.

Ehara et al. measured mRNA expression of FRP in synovial fluid from patients with RA and patients with OA. They found the mRNA expression of FRP was 2.3 fold higher in the RA patients than in the OA patients. Y. Ehara et al., Clin Exp Rheumatol 22, 707 (2004). Importantly, the authors stated that the FRP may exert a protective effect for joint destruction on synoviocytes.

Other groups have used mass spectroscopy to characterize the expression of a large number of genes to determine whether one or a combination of genes could be used for diagnostic purposes. For example, in WO 2005/032328, over 500 genes are disclosed as part of a mass screening. One of these genes (M285 in Table 1) is FSTL-1. Importantly, the data shows that the levels of FSTL-1 protein decreases in patients with erosive arthritis and also in patients with non-erosive arthritis as compared to healthy (normal) individuals (i.e., without arthritis).

Another publication, WO 2004/0018522 describes measurement of mRNA expression levels for a large number of genes to diagnose or predict multiple sclerosis. FSTL-1 appears in Table 3 and 9, however, only mRNA levels are measured and there is very limited disclosure that connects such expression in multiple sclerosis patients with arthritis (or, by extension, to other rheumatic diseases).

Finally, Miyamae et al. reported that FSTL-1 was a novel pro-inflammatory molecule with an unrecognized role in inflammation. T. Miyamae et al. J. Immunol. 177, 4758 (2006). Importantly, there was no disclosure in this reference that teaches or even suggests using protein levels of FSTL-1 as a biomarker for assessing disease severity in inflammatory diseases. As such, the invention describes a novel diagnostic biomarker that is capable of assessing disease severity in inflammatory and/or rheumatic diseases.

3. SUMMARY OF THE INVENTION

The invention provides methods and kits for diagnosing and assessing the severity of disease states for various inflammatory diseases by determining levels of follistatin-like protein-1 (FSTL-1). In certain non-limiting embodiments, the invention provides for methods and kits for diagnosing systemic inflammatory response syndrome (SIRS), infection or sepsis in a subject.

In particular non-limiting embodiments, the present invention provides for a method of diagnosing SIRS in a subject, comprising (i) determining the level of FSTL-1 in a sample from a subject manifesting (a) fever or a body temperature lower than normal; (b) tachycardia; (c) tachypnea; and (d) an elevated white blood cell count or neutropenia and/or greater than 10% immature band forms; (ii) comparing the level of FSTL-1 in the sample to a control level of FSTL-1 as determined by measuring the FSTL-1 level in a comparable sample from one or more healthy subject, and (iii) diagnosing SIRS where the serum level of FSTL-1 in the sample is at least 50% higher than the control level of FSTL-1.

In particular non-limiting embodiments, the present invention provides for a method of diagnosing sepsis in a subject, comprising (i) determining the level of FSTL-1 in a sample from a subject manifesting one or more of: an identified locus of infection, fever or a body temperature lower than normal; tachycardia; tachypnea; an elevated white blood cell count or neutropenia and/or greater than 10% immature band forms; (ii) comparing the level of FSTL-1 in the sample to a control level of FSTL-1 as determined by measuring the FSTL-1 level in a comparable sample from one or more healthy subject, and (iii) diagnosing sepsis where the serum level of FSTL-1 in the sample is at least 50% higher than the control level of FSTL-1.

4. BRIEF DESCRIPTION OF THE DRAWINGS

Figure 1B:
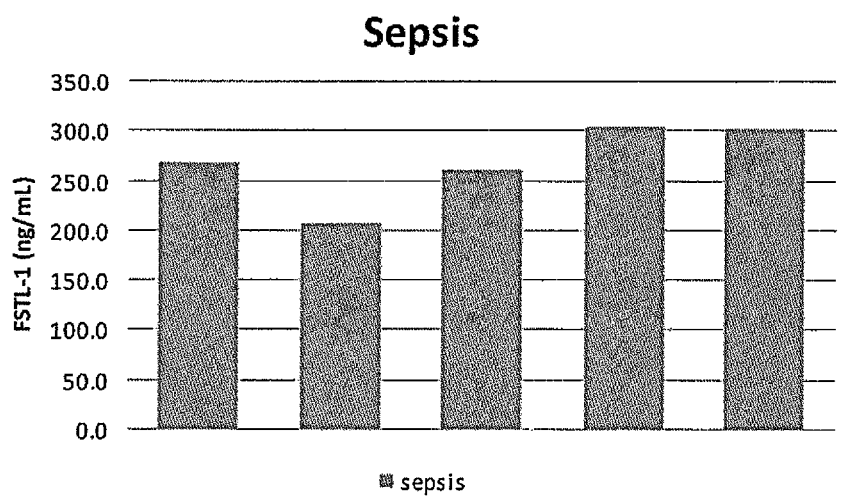

FIG. 1A-B. (A) Serum levels of FSTL-1 in five healthy human volunteers. (B) Serum levels of FSTL-1 in five humans diagnosed with sepsis.

Figure 2:
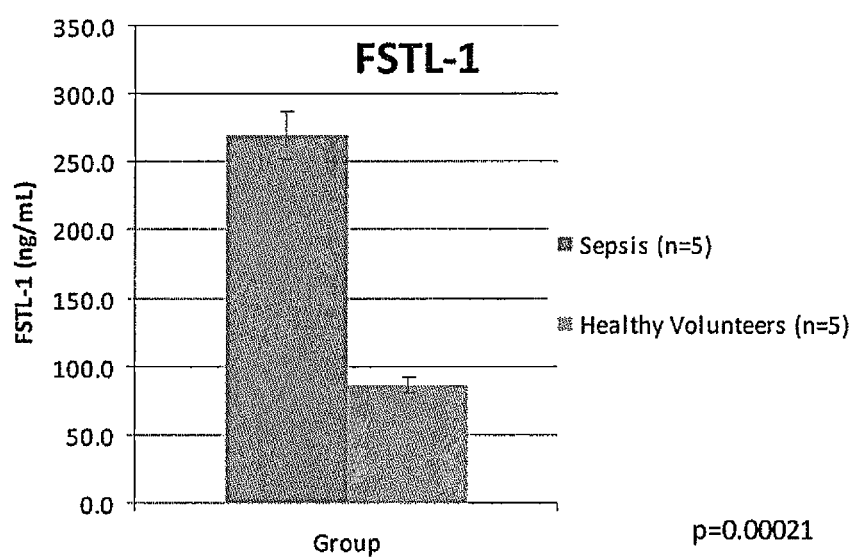

FIG. 2. Average serum levels of FSTL-1 in the healthy subjects and persons suffering from sepsis depicted in FIGS. 18A and 18B, respectively.

5. DETAILED DESCRIPTION OF THE INVENTION

The invention provides methods and kits for diagnosing and assessing the severity of SIRS, infection or sepsis by measuring protein levels of follistatin-like protein-1 (FSTL-1). The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, Molecular Cloning: A Laboratory Manual, second edition (Sambrook et al., 1989) and Molecular Cloning: A Laboratory Manual, third edition (Sambrook and Russel, 2001), (jointly referred to herein as "Sambrook"); Current Protocols in Molecular Biology (F. M. Ausubel et al., eds., 1987, including supplements through 2001); PCR: The Polymerase Chain Reaction, (Mullis et al., eds., 1994); Harlow and Lane (1988) Antibodies, A Laboratory Manual, Cold Spring Harbor Publications, New York; Harlow and Lane (1999) Using Antibodies: A Laboratory Manual Cold Spring Harbor Laboratory Press, Cold Spring Harbor, N.Y. (jointly referred to herein as "Harlow and Lane"), Beaucage et al. eds., and Current Protocols in Nucleic Acid Chemistry John Wiley & Sons, Inc., New York, 2000).

5.1 Definitions

FSTL-1 may be a human or non-human FSTL-1 protein. In one specific non-limiting example, human FSTL-1 protein has the sequence set forth in GenBank Accession No. AAH00055.1:

1 mwkrwlalal alvavawvra eeelrskski canvfcgagr ecavtekgep tcicieqckp
61 hkrpvcgsng ktylnhcelh rdacltgski qvdydghcke kksyspsasp vvcyqsnrde
121 lrrriiqwle aeiipdgwfs kgsnyseild kyfknfdngd srldsseflk fveqnetain
181 ittypdqenn kllrglcvda lielsdenad wklsfqeflk clnpsfnppe kkcaledety
241 adgaetevdc nrcvcacgnw vctamtcdgk nqkgaqtqte eemtryvqel qkhqetaekt
301 krvstkei (SEQ ID NO:1)

Additional specific non-limiting examples include mouse FSTL-1 (GenBank Accession No. EDK97964.1), rat FSTL-1 (GenBank Accession No. AAH87014.1), or cattle FSTL-1 (GenBank Accession No. AAI14759.1). Each of the sequences specified by GenBank Accession No. is hereby incorporated by reference in its entirety.

FSTL-1 nucleic acids include the genomic sequence and/or mRNA encoding FSTL-1. Non-limiting examples include human FSTL-1 mRNA (NCBI Ref. Seq. NM_007085.4), mouse FSTL-1 mRNA (NCBI Ref. Seq. NM_008047.5), rat FSTL-1 mRNA (NCBI Ref. Seq. NM_024369.2) or cattle FSTL-1 mRNA (NCBI Ref. Seq. NM_001017950.2). Each of the sequences specified by NCBI Reference No. is hereby incorporated by reference in its entirety.

The term "sample", as used herein, refers to a composition that is obtained or derived from an individual that contains a cellular and/or other molecular entity that is to be characterized and/or identified, for example based on physical, biochemical, chemical and/or physiological characteristics. In one embodiment, the sample is taken from the serum.

An "individual," also referred to as a "subject" is a vertebrate, such as mouse, and is preferably a mammal, more preferably a human. Mammals include, but are not limited to, humans, primates, farm animals, sport animals, rodents and domestic companion animals such as dogs and cats.

A "patient" refers to an "individual" or "subject" who is under the care of a treating physician. Patients can be of varying ages. In one embodiment, patients are humans. In another embodiment, patients are human children. In another embodiment, patients are human adults.

As used herein, "array" and "microarray" are interchangeable and refer to an arrangement of a collection of nucleotide sequences or proteins (and/or agents for detecting target protein(s)) in a centralized location. Arrays can be on a solid substrate, such as a glass slide, or on a semi-solid substrate, such as nitrocellulose membrane. The nucleotide sequences can be DNA, RNA, or any permutations thereof. The nucleotide sequences can also be partial sequences from a gene, primers, whole gene sequences, non-coding sequences, coding sequences, published sequences, known sequences, or novel sequences. In one embodiment, a protein array comprises FSTL-1. In another embodiment, the level of FSTL-1 protein can be determined using levels of mRNA of FSTL-1.

The term "polynucleotide" or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, refers to short, single stranded polynucleotides that are at least about seven nucleotides in length and less than about 250 nucleotides in length. Oligonucleotides may be synthetic. The terms "oligonucleotide" and "polynucleotide" are not mutually exclusive. The description above for polynucleotides is equally and fully applicable to oligonucleotides.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. In another example, one may use the results of a first analysis of a first individual (or patient) suspected of having a type of inflammatory disease and comparing with the results of a second analysis of a second individual who is known to not have such inflammatory disease (or alternatively, a standard) for correlation to determine the severity of the inflammatory disease in the first individual. With respect to the embodiment of FSTL-1 analysis or protocol, one may use the results of the FSTL-1 analysis or protocol to determine whether a specific therapeutic regimen should be performed depending on the severity of the disease and/or type of disease.

"Diagnosing" and "diagnosis"[refer to assigning a clinical category to a subject. Diagnosis may further include notifying the patient or another human person that the subject has been assigned a clinical category, for example a clinical category such as sepsis or systemic inflammatory response syndrome. Notification may, as non-limiting examples, be by electronic, written, or oral means.

The term "aiding diagnosis" is used herein to refer to methods that assist in making a clinical determination regarding the presence, degree or other nature, of a particular type of symptom or condition of inflammatory disease. For example, a method of aiding diagnosis of inflammatory disease can comprise measuring the amount or detecting the level of FSTL-1 in a biological sample from an individual. In another example, a method of aiding diagnosis of inflammatory disease can comprise measuring the amount or detecting the presence of FSTL-1 in a biological sample from an individual.

As used herein, "treatment" refers to clinical intervention in an attempt to alter the natural course of the individual or cell being treated, and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving remission or improved prognosis. In some embodiments, methods and compositions of the invention are useful in attempts to delay development of a disease or disorder.

A "medicament" is an active drug to treat a disease, disorder, and/or condition. In one embodiment, the disease, disorder, and/or condition is rheumatoid arthritis or its symptoms or side effects associated with treatment of rheumatoid arthritis.

"Systemic Inflammatory Response Syndrome" ("SIRS") is a clinical syndrome which may or may not be associated with infection and may, for example, but not by way of limitation, be associated with trauma, ischemia, hemorrhagic shock, immune-mediated organ injury, thermal injury, pancreatitis, or exogenous administration of inflammatory cytokines, among other disease states. Criteria for humans include (i) a body temperature greater than 38.3° C. or less than 36° C.; (ii) a heart rate greater than 90 beats/min; (iii) a respiratory rate greater than 20 breaths per minute and/or $PaCO_2$ less than 32 mm Hg; and (iv) a white blood cell count greater than $12 \times 10^9$ per liter or less than $4 \times 10^9$ per liter, and/or greater than 10% immature band forms. See Reidemann et al., 2003, J. Clin. Invest. 112(4): 460-467, p. 461 Table 1 and Members of ACCP/SCCM, 1992, Critical Care Med 20:864-874.

"Sepsis" is a clinical syndrome in which an infection is present together with two or more of (i)-(iv), as follows: (i) fever (e.g., for humans, a body temperature greater than 38.3° C.) or body temperature lower than normal (e.g. for humans, less than 36° C.); (ii) tachycardia (e.g. for humans, heart rate greater than 90 beats/min); (iii) tachypnea (e.g. for humans, respiratory rate greater than 20 breaths per minute and/or $PaCO_2$ less than 32 mm Hg); and/or (iv) elevated white blood cell count (e.g. for humans a white blood cell count greater than $12 \times 10^9$ per liter) or neutropenia (e.g. for humans less than $4 \times 10^9$ per liter), and/or greater than 10% immature band forms. See Reidemann et al., 2003, J. Clin. Invest. 112(4): 460-467, p. 461 Table 1.

"Septic shock" is sepsis associated with hypotension, for example, in a human, a systolic blood pressure of less than 90 mm Hg or a reduction of more than 40 mm Hg from base line, despite adequate fluid resuscitation, optionally along with the presence of perfusion abnormalities such as, but not limited to, lactic acidosis, oliguria, or an acute alteration in mental state. Vasopressor or inotropic agents may mask the hypotension associated with septic shock.

Reference to "about" a value or parameter herein includes (and describes) embodiments that are directed to that value or parameter per se. For example, description referring to "about X" includes description of "X."

5.2 Methods Of Diagnosis/Treatment

FSTL-1 is used as a biomarker by assessing the protein levels of FSTL-1 in a biological sample from a subject. The biological sample includes, but is not limited to, cells (e.g., peripheral blood mononuclear cells (PBMC), blood, plasma, serum, synovial fluid, broncheoalveolar lavage fluid, cerebrospinal fluid, pleural fluid and pericardial fluid. In one aspect of the invention, the assessment of expression is at the protein levels and not at the mRNA or nucleic acid level. In another aspect of the invention, the assessment of expression is at the nucleic acid levels (e.g., mRNA levels). Care should be taken to make sure that mRNA does not degrade so that accurate levels can be measured. It is to be understood that measurement of nucleic acid levels (e.g., mRNA levels) can be used as a surrogate or in place of protein levels throughout the specification.

The assessment of protein levels is routine and known to one of skill in the art. One possible method of measuring protein levels is by using immunoprecipitation (for example, using commercially available antibodies to FSTL-1/FRP/TSC-36) followed by Western blotting. However, sensitivity of the protein assay is important since there is a direct correlation between the level of FSTL-1 protein and the severity of the disease state. As such, ELISA (Enzyme Linked Immunosorbent Assay) or other more sensitive methods of measuring FSTL-1 protein expression is recommended. Polyclonal antibody toward FSTL-1 or one or more monoclonal antibody that binds to FSTL-1 may be used in any of the methods disclosed herein.

In any of the methods and kits disclosed herein, optionally, bacterially purified FSTL-1 (or any other organism capable of expressing FSTL-1 including insect cells infected with recombinant baculovirus expressing FSTL-1) can be used as a standard. In one aspect, the overexpression of FSTL-1 protein relative to normal individuals is predictive for that individual having at least one form of inflammatory disease.

In various non-limiting embodiments, FSTL-1 is measured by a method that comprises reacting FSTL-1 in a subject (e.g. patient or control) sample with a capture ligand to bind FSTL-1 to the capture ligand, and then directly or indirectly detecting the presence of FSTL-1 bound to the capture ligand.

In one set of non-limiting embodiments, FSTL-1 may be measured by the following method. For detection of human FSTL-1 in plasma, Nunc Immunomodule MaxiSorp F8 Framed ELISA plates may be coated with 5 ug/ml polyclonal anti-FSTL1 (AF1694; R&D Systems, Minneapolis, Minn.) in phosphate buffered saline (PBS) and incubated at 4° C. overnight. Plates may then be washed with PBS/0.05% Tween 20 and blocked for one hour with bovine serum albumin (BSA) buffer (1% BSA and 5% sucrose in PBS). Plates may then be washed again, and human plasma samples diluted 1:10 may be added. After washing, 2.5 ug/ml biotinylated monoclonal anti-FSTL1 (MAB 1694; R&D systems) may be added for 1 hour. Plates may then be washed again and incubated with Streptavidin-HRP conjugate at 0.25 ug/ml for 20 minutes. BD OptEIA TMB Substrate Reagent may then be added, and plates may be incubated for an additional hour, following which development may be stopped with addition of 1M $H_2SO_4$. Plate absorbance may be read on a microplate reader with dual measurement of 450 nm and 570 nm reference level. A titration of purified FSTL-1 may be used to generate a standard curve from which plasma concentration of samples may be calculated.

In alternative specific, non-limiting examples of the invention, FSTL-1 levels may be measured by the following method. For detection of human FSTL-1 in sera and synovial fluids, standard bind plates (Mesa Scale Discovery (MSD), Gaithersburg, Md.) may be coated with 0.2 µg per well goat anti-human FSTL1 (AF1694; R&D Systems, Minneapolis, Minn.) in 0.03% Triton-X100 overnight at 4° C. Plates may be washed with PBS/0.05% Tween-20 and blocked with MSD Human Serum Cytokine Assay Diluent for 1 hour. Human sera and synovial fluids, diluted 1:2 in MSD Human Serum Cytokine Assay Diluent, may be added overnight at 4° C. Plates may be washed and 0.5 µg/ml custom sulfo-tagged polyclonal rabbit anti-FSTL-1 may be added for 4 hours. Plates may be washed, 150 µl/well of 2× MSD Read Buffer may be added, and plates then may be imaged in a MSD SECTOR Imager 2400.

In particular non-limiting embodiments, the invention provides for a method of diagnosing SIRS in a subject, comprising (i) determining the level of FSTL-1 in a sample (for example, a blood sample or serum sample from a subject manifesting (a) either fever or body temperature lower than normal; (b) tachycardia; (c) tachypnea; and (d) an elevated white blood cell count or neutropenia and/or greater than 10% immature band forms; (ii) comparing the level of FSTL-1 in the sample to a control level of FSTL-1 as determined by measuring the FSTL-1 level in one or more comparable sample from one or more healthy subject, and (iii) diagnosing SIRS where the level of FSTL-1 in the sample is at least 50% higher (or at least 60% higher or at least 70% higher or at least 80% higher or at least 90% higher) than the control level of FSTL-1. For example, the level of FSTL-1 may be measured by ELISA. In certain embodiments, the subject has been determined to not suffer from an autoimmune disease which could alternatively explain the elevated FSTL-1.

In particular non-limiting embodiments, the invention provides for a method of diagnosing SIRS, comprising (i) obtaining a serum sample from a human subject manifesting (having) (a) a body temperature greater than 38.3° C. or less than 36° C.; (b) a heart rate greater than 90 beats/min; (c) a respiratory rate greater than 20 breaths per minute and/or $PaCO_2$ less than 32 mm Hg; and (d) a white blood cell count greater than $12\times10^9$ per liter or less than $4\times10^9$ per liter, and/or greater than 10% immature band forms; (ii) determining the level of FSTL-1 in the serum sample, and (iii) comparing the level of FSTL-1 in the serum sample to a control level of FSTL-1 as determined by measuring the FSTL-1 level in serum from one or more healthy human subject, where a serum level of FSTL-1 in the sample which is at least 50% higher or at least 60% higher or a least 70% higher or at least 80% higher or at least 90% higher or at least 100% higher than the control level of FSTL-1 indicates that the subject suffers from (has) SIRS. For example, the level of FSTL-1 may be measured by ELISA. In certain embodiments, the human subject has been determined to not suffer from an autoimmune disease, for example an inflammatory arthritis such as JRA/JIA, Kawasaki Disease, Lupus, etc. which could alternatively explain the elevated FSTL-1.

In particular non-limiting embodiments, the invention provides for a method of diagnosing SIRS in a human subject, comprising (i) determining the level of FSTL-1 in a serum sample from a human subject manifesting (a) a body temperature greater than 38.3° C. or less than 36° C.; (b) a heart rate greater than 90 beats/min; (c) a respiratory rate greater than 20 breaths per minute and/or $PaCO_2$ less than 32 mm Hg; and (d) a white blood cell count greater than $12\times10^9$ per liter or less than $4\times10^9$ per liter, and/or greater than 10% immature band forms and (ii) diagnosing SIRS where the serum level is greater than 120 ng/ml or greater than 150 ng/ml or greater than or equal to 200 ng/ml. For example, the level of FSTL-1 may be measured by ELISA. In certain embodiments, the human subject has been determined to not suffer from an autoimmune disease, for example an inflammatory arthritis such as JRA/JIA, Kawasaki Disease, Lupus, etc. which could alternatively explain the elevated FSTL-1.

In particular non-limiting embodiments, the invention provides for a method of diagnosing SIRS, comprising (i) obtaining a serum sample from a human subject manifesting (having) (a) a body temperature greater than 38.3° C. or less than 36° C.; (b) a heart rate greater than 90 beats/min; (c) a respiratory rate greater than 20 breaths per minute and/or $PaCO_2$ less than 32 mm Hg; and (iv) a white blood cell count greater than $12\times10^9$ per liter or less than $4\times10^9$ per liter, and/or greater than 10% immature band forms; (ii) determining the level of FSTL-1 in the serum sample, where a serum level of FSTL-1 greater than 120 ng/ml indicates that the subject suffers from (has) SIRS. For example, the level of FSTL-1 may be measured by ELISA. In certain embodiments, the human subject has been determined to not suffer from an autoimmune disease, for example an inflammatory arthritis such as JRA/JIA, Kawasaki Disease, Lupus, etc. which could alternatively explain the elevated FSTL-1.

In particular non-limiting embodiments, the invention provides for a method of diagnosing SIRS, comprising (i) obtaining a serum sample from a human subject manifesting (having) (a) a body temperature greater than 38.3° C. or less than 36° C.; (b) a heart rate greater than 90 beats/min; (c) a respiratory rate greater than 20 breaths per minute and/or $PaCO_2$ less than 32 mm Hg; and (iv) a white blood cell count greater than $12\times10^9$ per liter or less than $4\times10^9$ per liter, and/or greater than 10% immature band forms; (ii) determining the level of FSTL-1 in the serum sample, where a serum level of FSTL-1 greater than 150 ng/ml indicates that the subject suffers from (has) SIRS. For example, the level of FSTL-1 may be measured by ELISA. In certain embodiments, the human subject has been determined to not suffer from an autoimmune disease, for example an inflammatory arthritis such as JRA/JIA, Kawasaki Disease, Lupus, etc. which could alternatively explain the elevated FSTL-1.

In particular non-limiting embodiments, the invention provides for a method of diagnosing SIRS, comprising (i) obtaining a serum sample from a human subject manifesting (having) (a) a body temperature greater than 38.3° C. or less than 36° C.; (b) a heart rate greater than 90 beats/min; (c) a respiratory rate greater than 20 breaths per minute and/or $PaCO_2$ less than 32 mm Hg; and (iv) a white blood cell count greater than $12\times10^9$ per liter or less than $4\times10^9$ per liter, and/or greater than 10% immature band forms; (ii) determining the level of FSTL-1 in the serum sample, where a serum level of FSTL-1 greater than or equal to 200 ng/ml indicates that the subject suffers from (has) SIRS. For example, the level of FSTL-1 may be measured by ELISA. In certain embodiments, the human subject has been determined to not suffer from (e.g., has not been previously diagnosed with) an autoimmune disease, for example an inflammatory arthritis such as JRA/JIA, Kawasaki Disease, Lupus, etc. which could alternatively explain the elevated FSTL-1.

In particular non-limiting embodiments of the invention, FSTL-1 may be used as a marker of bacterial, viral, parasite or fungal sepsis. For example, but not by way of limitation, the level of FSTL-1 may be a serum level measured by collecting a serum sample from the test subject and then determining, in the serum sample, the level of FSTL-1. In particular non-limiting embodiments, a serum level of FSTL-1 in a test subject manifesting one or more (or at least two, or at least three) indicia of infection, where the serum level of FSTL-1 of the test subject is at least 50% higher or at least 60% higher or a least 70% higher or at least 80% higher or at least 90% higher or at least 100% higher, than a control serum level of FSTL-1 established in one or more healthy subject(s), indicates that the subject is suffering from sepsis. Indicia of infection include, but are not limited to, an elevated or decreased body temperature (relative to normal) (e.g., in humans, greater than 38.3° C. or less than 36° C.); tachycardia (e.g., in humans, a heart rate greater than 90 beats/min); tachypnea (e.g. in humans, a respiratory rate greater than 20 breaths per minute and/or $PaCO_2$ less than 32 mm Hg); elevated white blood cell count (e.g. in humans, a white blood cell count greater than $12\times10^9$ per liter), low white blood cell count (e.g. in humans, less than 4×109 per liter); increased band forms (e.g. in humans, greater than 10% immature band forms), identified locus of infection (e.g. infected wound or other lesion, abscess, septic joint, endocarditis, septicemia (infection in the blood), urinary tract infection, pneumonia, perforated bowel, etc.), immunosuppression (e.g. secondary to chemotherapy (e.g. bone marrow toxic agents or chemical immunosuppressants) and/or disease such as malignancy, immunosuppressive viral infection (such as Human Immunodeficiency Virus infection)), elevated levels of inflammatory cytokines (including, but not limited to, tumor necrosis factor alpha, interleukin-1, interleukin-2, interleukin 6, interleukin-12), elevated heart rate (e.g., in humans, >90 beats/minute at rest, meningitis, and/or rash. In particular non-limiting embodiments, the FSTL-1 is measured using an ELISA assay. In particular non-limiting embodiments, the subject is a human. In certain non-limiting embodiments, the subject is a human subject manifesting two or more of (i)-(iv), as follows: (i) a body temperature greater than 38.3° C. or less than 36° C.; (ii) heart rate greater than 90 beats/min; (iii) respiratory rate greater than 20 breaths per minute and/or $PaCO_2$ less than 32 mm Hg; and (iv) a white blood cell count greater than $12\times10^9$ per liter or less than $4\times10^9$ per liter, and/or greater than 10% immature band forms.

In particular, non-limiting embodiments, the invention provides for a method of diagnosing sepsis in a subject, comprising (i) determining the level of FSTL-1 in a serum sample from a subject manifesting one or more (or at least two, or at least three) of: an identified locus of infection, fever or a body temperature lower than normal; tachycardia; tachypnea; an elevated white blood cell count or neutropenia and/or greater than 10% immature band forms; (ii) comparing the level of FSTL-1 in the serum sample to a control level of FSTL-1 as determined by measuring the FSTL-1 level in serum from one or more healthy subject, and (iii) diagnosing sepsis where a serum level of FSTL-1 in the sample is at least 50% higher (or at least 60% higher or at least 70% higher or at least 80% higher or at least 90% higher) than the control level of FSTL-1.

In a specific, non-limiting embodiment, the invention provides for a method of diagnosing sepsis, comprising (i) obtaining, from a human subject manifesting one or more (or at least two, or at least three) indicia of infection, a serum sample; (ii) determining the level of FSTL-1 in the serum sample, and (iii) comparing the level of FSTL-1 in the serum sample to a control level of FSTL-1 as determined by measuring the FSTL-1 level in serum from one or more healthy human subject, where a serum level of FSTL-1 in the sample which is at least 50% higher or at least 60% higher or a least 70% higher or at least 80% higher or at least 90% higher or at least 100% higher than the control level of FSTL-1 indicates that the subject suffers from (has) sepsis. For example, the level of FSTL-1 may be measured by ELISA. In certain non-limiting embodiments, the subject is a human subject manifesting two or more of (i)-(iv), as follows: (i) a body temperature greater than 38.3° C. or less than 36° C.; (ii) heart rate greater than 90 beats/min; (iii) respiratory rate greater than 20 breaths per minute and/or $PaCO_2$ less than 32 mm Hg; and (iv) a white blood cell count greater than $12 \times 10^9$ per liter or less than $4 \times 10^9$ per liter, and/or greater than 10% immature band forms. In certain embodiments, the human subject has been determined to not suffer from an autoimmune disease, for example an inflammatory arthritis such as JRA/JIA, Kawasaki Disease, Lupus, etc. which could alternatively explain the elevated FSTL-1.

In particular non-limiting embodiments, the invention provides for a method of diagnosing sepsis in a human subject, comprising (i) determining the level of FSTL-1 in a serum sample from a human subject manifesting one or more (or at least two, or at least three) indicia of infection and (ii) diagnosing sepsis where the serum level of FSTL-1 is greater than 120 ng/ml or greater than 150 ng/ml or greater than or equal to 200 ng/ml.

In a specific, non-limiting embodiment, the invention provides for a method of diagnosing sepsis, comprising (i) obtaining, from a human subject manifesting one or more (or at least two, or at least three) indicia of infection, a serum sample; and (ii) determining the level of FSTL-1 in the serum sample, where a serum level of FSTL-1 greater than 120 ng/ml indicates that the subject suffers from (has) sepsis. For example, the level of FSTL-1 may be measured by ELISA. In certain non-limiting embodiments, the subject is a human subject manifesting two or more of (i)-(iv), as follows: (i) a body temperature greater than 38.3° C. or less than 36° C.; (ii) heart rate greater than 90 beats/min; (iii) respiratory rate greater than 20 breaths per minute and/or $PaCO_2$ less than 32 mm Hg; and (iv) a white blood cell count greater than $12 \times 10^9$ per liter or less than $4 \times 10^9$ per liter, and/or greater than 10% immature band forms. In certain embodiments, the human subject has been determined to not suffer from an autoimmune disease, for example JRA/JIA, Kawasaki Disease, Lupus, etc. which could alternatively explain the elevated FSTL-1. In certain non-limiting embodiments, the subject does not have inflammatory arthritis.

In a specific, non-limiting embodiment, the invention provides for a method of diagnosing sepsis, comprising (i) obtaining, from a human subject manifesting one or more (or at least two, or at least three) indicia of infection, a serum sample; and (ii) determining the level of FSTL-1 in the serum sample, where a serum level of FSTL-1 greater than 150 ng/ml indicates that the subject suffers from (has) sepsis. For example, the level of FSTL-1 may be measured by ELISA. In certain non-limiting embodiments, the subject is a human subject manifesting two or more of (i)-(iv), as follows: (i) a body temperature greater than 38.3° C. or less than 36° C.; (ii) heart rate greater than 90 beats/min; (iii) respiratory rate greater than 20 breaths per minute and/or $PaCO_2$ less than 32 mm Hg; and (iv) a white blood cell count greater than $12 \times 10^9$ per liter or less than $4 \times 10^9$ per liter, and/or greater than 10% immature band forms. In certain embodiments, the human subject has been determined to not suffer from an autoimmune disease, for example JRA/JIA, Kawasaki Disease, Lupus, etc. which could alternatively explain the elevated FSTL-1. In certain non-limiting embodiments, the subject does not have inflammatory arthritis.

In a specific, non-limiting embodiment, the invention provides for a method of diagnosing sepsis, comprising (i) obtaining, from a human subject manifesting one or more (or at least two, or at least three) indicia of infection, a serum sample; and (ii) determining the level of FSTL-1 in the serum sample, where a serum level of FSTL-1 greater than or equal to 200 ng/ml indicates that the subject suffers from (has) sepsis. For example, the level of FSTL-1 may be measured by ELISA. In certain non-limiting embodiments, the subject is a human subject manifesting two or more of (i)-(iv), as follows: (i) a body temperature greater than 38.3° C. or less than 36° C.; (ii) heart rate greater than 90 beats/min; (iii) respiratory rate greater than 20 breaths per minute and/or $PaCO_2$ less than 32 mm Hg; and (iv) a white blood cell count greater than $12 \times 10^9$ per liter or less than $4 \times 10^9$ per liter, and/or greater than 10% immature band forms. In certain embodiments, the human subject has been determined to not suffer from an autoimmune disease, for example JRA/JIA, Kawasaki Disease, Lupus, etc. which could alternatively explain the elevated FSTL-1. In certain non-limiting embodiments, the subject does not have inflammatory arthritis.

In certain non-limiting embodiments, the invention provides for a method of treating a subject comprising a diagnostic method set forth above and further including initiating or recommending a treatment for sepsis, for example, administering an antibiotic. Suitable antibiotics are known in the art and would include, but not be limited to, a penicillin-like antibiotic such as penicillin or ampicillin, vancomycin, cefazolin, ceftriaxone, piperacillin/tazobactam, gentamycin, tobramycin, azithromycin, meropenem, doxycycline, minocycline, trimethoprim/sulfamethoxazole, linezolid, clindamycin, daptomycin, teicoplanin, acyclovir, ketoconazole, or combinations thereof. An antibiotic used to treat a septic patient may be based on the sensitivity profile of the organism causing the sepsis.

A wide variety of organisms can cause sepsis in humans. Non-limiting examples include *Staphylococcus aureus*, methicillin-resistant *Staphylococcus aureus* (MRSA), *Streptococcus pneumoniae*, *Pseudomonas aeruginosa*, *Escherichia coli*, *Klebsiella pneumoniae*, *Bacteroides fragilis*, *Enterococcus*, *Neiserria meningitidis*, and *Candida albicans*.

In certain non-limiting embodiments, the invention provides for a method of treating a subject comprising a diagnostic method set forth above and further including initiating or recommending a treatment for SIRS or sepsis including more frequent blood pressure monitoring for the onset of hypotension and should hypotension occur consequent administration of one or more hypertensive agent such as a vasopressor and/or inotropic agent, for example, but not limited to, epinephrine, noradrenaline, phenylephrine, dobutamine, dopamine, midodrine, digoxin, and/or amrinone.

The methods of this invention are also used to monitor the progression of a treatment plan for infectious disease. FSTL-1 protein levels are assessed prior the start of any treatment program. Once the treatment plan starts, FSTL-1 levels are continually monitored, for example by testing the individual's serum, to determine if the individual is responding to the treatment. In such manner, one can determine if the treatment plan is effective and if not, utilize a different treatment plan.

Where SIRS, or infection, or sepsis has been diagnosed, the response of the condition to treatment may be monitored by re-assessing the level of FSTL-1. For example, where treatment is successful, the level of FSTL-1 is expected to decrease, and where the subject's condition worsens, the level of FSTL-1 is expected to increase. For example, the magnitude of the change may be by at least about 20% or at least 30% or at least 40% or at least 50% relative to the previously measured value.

5.3 Kits

Arrays and microarrays which comprise FSTL-1 are described herein for assessing the severity of inflammatory diseases, including SIRS and infectious diseases as discussed above. Methods of making arrays are well-known in the art and as such, do not need to be described in detail here.

Protein arrays are well-known to those in the art. Various types of protein arrays (e.g., analytical microarrays, functional microarrays, and reverse phase microarrays) may be used to detect levels of FSTL-1 protein. Accordingly, in one aspect of the invention, a protein array comprising agents, such as capture agents (e.g., antibodies, aptamers, affibodies, peptides, full-length functional proteins or protein domains, tissue lysates for reverse phase microarrays), that bind to and/or interact with FSTL-1 is used as a diagnostic. Protein arrays may be used to detect FSTL-1 in combination with other proteins of interest (e.g., IL-1.beta., IFN-.gamma., TNF-.alpha., IL-6, etc.) on the same array, which may be useful for diagnostic purposes in the context of inflammatory diseases.

In another embodiment, the array is an array probe of nucleic acids, such as a DNA chip, in which FSTL-1 is represented. A variety of different array formats are known in the art, with a wide variety of different probe structures, substrate compositions and attachment technologies. Representative array structures of interest include those described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; WO 95/21265; WO 96/31622; WO 97/10365; WO 97/27317; EP 373 203; and EP 785 280.

The invention provides composition comprising the reagents and/or materials needed to measure FSTL-1 levels in a biological sample. In one embodiment, bacterially purified FSTL-1 is provided as a standard in the kit. In another embodiment, FSTL-1 is purified from insect cells in which a recombinant baculovirus expressing FSTL-1 had been introduced. Instructions for conducting the determination of FSTL-1 protein levels are optionally included. In another embodiment, instructions for how to correlate the levels of FSTL-1 protein with disease severity are optionally included.

In another embodiment, the invention provides for kits comprising an array which comprises FSTL-1. As discussed infra, the array may be a protein array or a surrogate for detecting protein level (e.g., nucleic acid array). The kits of the subject invention may include the above described arrays. The kits may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g., hybridization and washing buffers, prefabricated probe arrays, labeled probe purification reagents and components, like spin columns, etc., signal generation and detection reagents, e.g., streptavidin-alkaline phosphatase conjugate, chemifluorescent or chemiluminescent substrate, and the like.

In non-limiting embodiments, the present invention provides for a kit comprising an anti-FSTL-1 antibody, which may be a polyclonal or a monoclonal antibody. Said antibody may optionally be detectably labeled and/or binding of said antibody to FSTL-1 may be indirectly detected for example by a labeled secondary antibody directed toward said first anti-FSTL-1 antibody. A detectable label may be a radioactive, a fluorescent, or a colorimetric label as is known in the art. Said secondary antibody may also optionally be included in the kit. The kit may optionally further comprise a sample of FSTL-1 standard which may be used to determine the concentration of FSTL-1 in a subject (patient) sample. The kit may optionally further comprise a control sample or a facsimile thereof which may be used to determine whether FSTL-1 in a subject (sample) is elevated or not. The kit may optionally further comprise a description that includes a control level of FSTL-1 and/or disclosure that, in a human, a FSTL-1 serum level which is greater than 120 ng/ml or a value which is greater than 150 ng/ml or a value which is greater than or equal to 200 ng/ml indicates a diagnosis of SIRS or sepsis.

In addition to the above components, the kits will further include instructions for practicing the methods and arrays described herein. These instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the Internet to access the information at a removed site. Any convenient means may be present in the kits.

Also provided are reagents and kits thereof for practicing one or more of the above described methods. The subject reagents and kits thereof may vary greatly. Reagents of interest include reagents specifically designed for use in production of the above described FSTL-1 protein.

5.4 Computer-Readable Media Comprising FSTL-1

The invention also contemplates computer readable media that comprises information on FSTL-1. Such media can contain all of part of the data for levels of FSTL-1 and other medical information that would be helping in diagnosing or aiding in the diagnosis of inflammatory diseases as described herein.

Program Products/Systems: Another aspect of the invention provides a program product (i.e., software product) for use in a computer device that executes program instructions recorded in a computer-readable medium to perform statistical calculations relating to FSTL-1 levels for diagnostic purposes.

In one embodiment, the program product comprises: a recordable medium; and a plurality of computer-readable instructions executable by the computer device to analyze data from the array hybridization steps, to transmit array hybridization from one location to another, or to evaluate genome-wide location data between two or more genomes. Computer readable media include, but are not limited to, CD-ROM disks (CD-R, CD-RW), DVD-RAM disks, DVD-RW disks, floppy disks and magnetic tape.

A related aspect of the invention provides kits comprising the program products described herein. The kits may also optionally contain paper and/or computer-readable format instructions and/or information, such as, but not limited to, information on protein or nucleic acid microarrays, on tutorials, on experimental procedures, on reagents, on related products, on available experimental data, on using kits, on agents for treating inflammatory diseases, including their toxicity, and on other information. The kits optionally also contain in paper and/or computer-readable format information on minimum hardware requirements and instructions for running and/or installing the software.

It will be apparent to those of ordinary skill in the art that methods involved in the present invention may be embodied in a computer program product that includes a computer usable and/or readable medium. For example, such a computer usable medium may consist of a read only memory device, such as a CD ROM disk or conventional ROM devices, or a random access memory, such as a hard drive device or a computer diskette, having a computer readable program code stored thereon.

The following examples are given to illustrate aspects of the invention. They are not meant to limit the invention in any manner.

6. EXAMPLE 1

Assessing FTSL-1 Protein Levels

Assessing the protein levels of either mouse FSTL-1 (mFSTL-1) or human FSTL-1 (hFSTL-1) by ELISA was accomplished using the following materials and methods:

Solutions: Coating Buffer—PBS pH 7.4; Blocking Buffer—PBS with 1% BSA, 5% sucrose, and 0.05% Tween 20; Diluent—TBS pH 7.3 (20 nM Tris, 150 mM NaCl) with 0.1% BSA, 0.05% Tween 20; and Wash Buffer—PBS 0.05%, Tween-20.

Plate: Catalog #468667 or 434797 from Nunc Immunomodule, MaxiSorp™ F8 framed.

1. Coating.fwdarw.Coat the plate with 2 µg/ml of polyclonal goat anti-human FSTL-1 at 100 .mu.1/well (R&D #AF 1694=0.1 mg/ml) or polyclonal goat anti-mouse FSTL-1 (R&D #AF 1738) at 4 degrees C. overnight (20 µl+1 ml of PBS).
2. Wash three times with Wash Buffer.
3. Block the plate with 300 µl/well of blocking buffer at least 1 hour at room temperature.
4. Wash three times with Wash Buffer.
5. Sample loading Load samples or bacterially purified human FSTL-1 100 µl/well (diluted with Diluent Buffer) in duplicate and incubate overnight at 4 degrees C. The standard used for hFSTL-1 was bacterially purified hFSTL-1 at 10000 ng/mL (490 µl dil.buffer+10 µL standard=200 ng/ml). For mFSTL-1, bacterially purified mFSTL-1 at 10000 ng/mL (490 µl dil.buffer+10 .mu.L standard=200 ng/ml) was used. A method to produce FSTL-1 in bacteria is provided in Example 7.
6. Wash plate three times.
7. Add 100 µl of first monoclonal rat anti-FSTL-1 mAb 1.25 µg/ml incubate for 1 hr at RT (20-25 degrees C.) (R&D eat #MAB 1738, 500 µg/ml). Dilute 1:400 to a final concentration of 1.25 µg/ml.
8. Wash three times with Wash Buffer.
9. Add 100 µl of second polyclonal goat anti rat-HRP (KPL #04-16-02; 0.1 mg/ml; at 4.degree. C., Box #12) incubate for 1 hr. at room temperature (20-25 degrees C.). Diluted 1:500; final concentration will be 0.2 µg/ml.
10. Wash three times with Wash Buffer.
11. Substrate; ABTS mixture same dose of ARTS (A) and (B) less than 20 minutes before using and add 100 µl/well of mixed substrate.
12. Do OD reading at 405 TIM to determine absorbance.

7. EXAMPLE 2

Serum FSTL-1 Increases in Sepsis

Serum levels of FSTL-1 were measured in normal human volunteers as well as human patients fulling the ACCP/SCCM criteria for sepsis. Measurement was performed by ELISA assay.

The results of these studies are shown in Table 1 below. As depicted in FIGS. 1A, 1B and 2, the serum levels of FSTL-1 were significantly higher in sepsis patients. In healthy patients the average FSTL-1 serum level was 86.6675±5.97 SEM, whereas in sepsis patients the average FSTL-1 level was 268.9±17.64 SEM.

TABLE 1

| FSTL-1 ng/mL | Standard 1 | Standard 2 | Stand Avg | % Diff | | |
|---|---|---|---|---|---|---|
| 50 | 1.25 | 1.226 | 1.238 | 0.019 | | |
| 25 | 0.592 | 0.515 | 0.554 | 0.139 | slope | slope (all) |
| 12.5 | 0.341 | 0.296 | 0.319 | 0.141 | 0.023057 | 0.02214751 |
| 6.25 | 0.209 | 0.174 | 0.192 | 0.183 | intercept | intercept |
| 3.125 | 0.19 | 0.157 | 0.174 | 0.190 | 0.048271 | 0.080293103 |
| 1.5625 | 0.153 | 0.121 | 0.137 | 0.234 | r2 | r2 |
| 0.78125 | 0.162 | 0.133 | 0.148 | 0.197 | 0.98775 | 0.984583416 |
| 0 | 0.143 | 0.134 | 0.139 | 0.065 | | |

| | Standard 1 | Standard 2 | Stand Avg | % Diff | FSTL-1 | FSTL-1 ng/mL | Avg | SEM |
|---|---|---|---|---|---|---|---|---|
| HV 3 T0 | 0.28 | 0.255 | 0.268 | 0.093 | 9.508144 | 95.1 | 86.6675 | 5.97 |
| HV 5 T0 | 0.276 | 0.278 | 0.277 | 0.007 | 9.920166 | 99.2 | | |
| HV 8 T0 | 0.24 | 0.236 | 0.238 | 0.017 | 8.228705 | 82.3 | | |
| HV 13 T0 | 0.198 | 0.201 | 0.200 | 0.015 | 6.558929 | 65.6 | | |
| HV 21 T0 | 0.258 | 0.259 | 0.259 | 0.004 | 9.117807 | 91.2 | | |
| S 9 T0 | 0.659 | 0.672 | 0.666 | 0.020 | 26.76972 | 267.7 | 268.9 | 17.64 |
| S 10 T0 | 0.532 | 0.524 | 0.528 | 0.015 | 20.80624 | 208.1 | | |
| S 11 T0 | 0.64 | 0.66 | 0.650 | 0.031 | 26.09747 | 261.0 | | |
| S 12 T0 | 0.743 | 0.761 | 0.752 | 0.024 | 30.52129 | 305.2 | | |
| S 17 T0 | 0.745 | 0.747 | 0.746 | 0.003 | 30.26107 | 302.6 | | |
| yury-cntrl | 0.249 | 0.243 | 0.246 | 0.024 | 8.575672 | 85.8 | | |

T test (Sepsis vs Healthy volunteers)
0.000211

8. References Bibliography

1. Thornton, S., D. Sowders, B. Aronow, D. P. Witte, H. I. Brunner, E. H. Giannini, and R. Hirsch. 2002. DNA microarray analysis reveals novel gene expression profiles in collagen-induced arthritis. Clin Immunol 105:155-168.
2. Shibanuma, M., J. Mashimo, A. Mita, T. Kuroki, and K. Nose. 1993. Cloning from a mouse osteoblastic cell line of a set of transforming-growth-factor-beta 1-regulated genes, one of which seems to encode a follistatin-related polypeptide. Eur J Biochem 217:13-19.
3. Tanaka, M., S. Ozaki, F. Osakada, K. Mori, M. Okubo, and K. Nakao. 1998. Cloning of follistatin-related protein as a novel autoantigen in systemic rheumatic diseases. Int Immunol 10:1305-1314.
4. Kawabata, D., M. Tanaka, T. Fujii, H. Umehara, Y. Fujita, H. Yoshifuji, T. Mimori, and S. Ozaki. 2004. Ameliorative effects of follistatin-related protein/TSC-36/FSTL1 on joint inflammation in a mouse model of arthritis. Arthritis Rheum 50:660-668.
5. Tanaka, M., S. Ozaki, D. Kawabata, M. Kishimura, F. Osakada, M. Okubo, M. Murakami, K. Nakao, and T. Mimori. 2003. Potential preventive effects of follistatin-related protein/TSC-36 on joint destruction and antagonistic modulation of its autoantibodies in rheumatoid arthritis. Int Immunol 15:71-77.
6. Miyamae, T., A. D. Marinov, D. Sowders, D.C. Wilson, J. Devlin, R. Boudreau, P. Robbins, and R. Hirsch. 2006. Follistatin-like protein-1 is a novel proinflammatory molecule. J Immunol 177:4758-4762.
7. Hardy, S., M. Kitamura, T. Harris-Stansil, Y. Dai, and M. L. Phipps. 1997. Construction of adenovirus vectors through Cre-lox recombination. J Virol 71:1842-1849.
8. Hughes, C., J. A. Wolos, E. H. Giannini, and R. Hirsch. 1994. Induction of T cell anergy in an experimental model of autoimmunity using non-mitogenic anti-CD3 monoclonal antibody. J Immunol 153:3319-3325,
9. Sudo, H., H. A. Kodama, Y. Amagai, S. Yamamoto, and S. Kasai. 1983. In vitro differentiation and calcification in a new clonal osteogenic cell line derived from newborn mouse calvaria. J Cell Biol 96:191-198.
10. Shin, S. R., N. Sanchez-Velar, D. H. Sherr, and G. E. Sonenshein. 2006. 7,12-dimethylbenz(a)anthracene treatment of a c-rel mouse mammary tumor cell line induces epithelial to mesenchymal transition via activation of nuclear factor-kappaB. Cancer Res 66:2570-2575.
11. Kubo, R. T., W. Born, J. W. Kappler, P. Marrack, and M. Pigeon. 1989. Characterization of a monoclonal antibody which detects all murine .alpha.beta. T cell receptors. J Immunol 142:2736-2742.
12. Massague, J., and Y. G. Chen. 2000. Controlling TGF-beta signaling. Genes Dev 14:627-644.
13. Moustakas, A. 2002. Smad signalling network. J Cell Sci 115:3355-3356.
14. Kim, E. Y., and H. S. Teh. 2001. TNF type 2 receptor (p75) lowers the threshold of T cell activation. J Immunol 167: 6812-6820.
15. Yamada, A., A. D. Salama, N. Najafian, H. Auchincloss, Jr., and M. H. Sayegh. 2001. TNF:TNF-R costimulatory pathways in transplantation. Transplant Proc 33:3070-3071.
16. Brown, K., S. Gerstberger, L. Carlson, G. Franzoso, and U. Siebenlist. 1995. Control of I kappa B-alpha proteolysis by site-specific, signal-induced phosphorylation. Science 267:1485-1488.
17. Ehara, Y., D. Sakurai, N. Tsuchiya, K. Nakano, Y. Tanaka, A. Yamaguchi, and K. Tokunaga. 2004. Follistatin-related protein gene (FRP) is expressed in the synovial tissues of rheumatoid arthritis, but its polymorphisms are not associated with genetic susceptibility. Clin Exp Rheumatol 22:707-712.
18. Kwak, H. B., H. Ha, H. N. Kim, J. H. Lee, H. S. Kim, S. Lee, H. M. Kim, J. Y. Kim, H. H. Kim, Y. W. Song, and Z. H. Lee. 2008. Reciprocal cross-talk between RANKL and interferon-gamma-inducible protein 10 is responsible for bone-erosive experimental arthritis. Arthritis Rheum 58:1332-1342.
19. Gett, A. V., F. Sallusto, A. Lanzavecchia, and J. Geginat. 2003. T cell fitness determined by signal strength. Nat Immunol 4:355-360.
20. van Stipdonk, M. J., G. Hardenberg, M. S. Bijker, E. E. Lemmens, N. M. Droin, D. R. Green, and S. P. Schoenberger. 2003. Dynamic programming of CD8+ T lymphocyte responses. Nat Immunol 4:361-365.
21, Thornton, S., G. P. Boivin, K. N. Kim, F. D. Finkelman, and R. Hirsch. 2000. Heterogeneous effects of IL-2 on collagen-induced arthritis. J Immunol 165:1557-1563.
22. Thornton, S., K. A. Kuhn, F. D. Finkelman, and R. Hirsch. 2001. NK cells secrete high levels of IFN-gamma in response to in vivo administration of IL-2. European journal of immunology 31:3355-3360.
23. Chu, C. Q., Z. Song, L. Mayton, B. Wu, and P. H. Wooley. 2003. IFNgamma deficient C57BL/6 (H-2b) mice develop collagen induced arthritis with predominant usage of T cell receptor Vbeta6 and Vbeta8 in arthritic joints. Annals of the rheumatic diseases 62:983-990. Sequence CWU 1

Throughout this specification, various patents, patent applications and other types of publications (e.g., journal articles) are referenced. The disclosure of all patents, patent applications, and publications cited herein are hereby incorporated by reference in their entirety for all purposes.

I claim:
1. A method of diagnosing sepsis in a subject, comprising (i) determining the level of follistatin-like protein-1 in a serum sample from a subject manifesting one or more of: an identified locus of infection, fever or a body temperature lower than normal; tachycardia; tachypnea; an elevated white blood cell count or neutropenia and/or greater than 10% immature band forms; (ii) comparing the level of follistatin-like protein-1 in the serum sample to a control level of follistatin-like protein-1 as determined by measuring the follistatin-like protein-1 level in serum from one or more healthy subjects, and (iii) diagnosing sepsis where a serum level of follistatin-like protein-1 in the sample of the subject is at least 50% higher than the control level of follistatin-like protein-1 indicates that the subject has sepsis.
2. A method of diagnosing sepsis in a human subject, comprising (i) determining the level of follistatin-like protein-1 in a serum sample from a human subject manifesting one or more of: an identified locus of infection, a body temperature greater than 38.3° C. or less than 36° C.; a heart rate greater than 90 beats/min; a respiratory rate greater than 20 breaths per minute and/or $PaCO_2$ less than 32 mm Hg; a white blood cell count greater than $12 \times 10^9$ per liter or less than $4 \times 10^9$ per liter, and/or greater than 10% immature band forms; (ii) comparing the level of follistatin-like protein-1 in the serum sample to a control level of follistatin-like protein-1 as determined by measuring the follistatin-like protein-1 level in serum from one or more healthy human subjects, and (iii) diagnosing sepsis where a serum level of follistatin-like protein-1 in the sample of the subject is at least 50% higher than the control level of follistatin-like protein-1 indicates that the subject has sepsis.
3. The method of claim 1 or 2, where the level of follistatin-like protein-1 is determined by enzyme linked immunosorbent assay.

4. The method of claim 1, 2 or 3, where the human subject has been determined to not suffer from an autoimmune disease.

5. The method of claim 2, 3 or 4, where the human subject has not previously been diagnosed with autoimmune arthritis.

6. A method of diagnosing sepsis in a human subject, comprising (i) determining the level of follistatin-like protein-1 in a serum sample from a human subject manifesting one or more of: an identified locus of infection, a body temperature greater than 38.3° C. or less than 36° C.; a heart rate greater than 90 beats/min; a respiratory rate greater than 20 breaths per minute and/or $PaCO_2$ less than 32 mm Hg; a white blood cell count greater than $12 \times 10^9$ per liter or less than $4 \times 10^9$ per liter, and/or greater than 10% immature band forms; and (ii) diagnosing sepsis where the serum level of the subject is above 120 ng/ml.

7. The method of claim 6, where the level of follistatin-like protein-1 is determined by enzyme linked immunosorbent assay.

8. The method of claim 6 or 7, where the human subject has been determined to not suffer from an autoimmune disease.

9. The method of claim 6, 7 or 8, where the human subject has not previously been diagnosed with autoimmune arthritis.

10. The method of claim 6, 7, 8 or 9 where the level of follistatin-like protein-1 in the serum sample is greater than 150 ng/ml.

11. The method of claim 6, 7, 8 or 9 where the level of follistatin-like protein-1 in the serum sample is greater than or equal to 200 ng/ml.

\* \* \* \* \*